United States Patent
Harter et al.

(10) Patent No.: US 7,613,619 B1
(45) Date of Patent: Nov. 3, 2009

(54) METHOD FOR IDENTIFYING ALLERGENS AND OTHER INFLUENCING AGENTS THAT MAY CAUSE A REACTION

(76) Inventors: Michael R. Harter, 510 N. 4th Ave., Sturgeon Bay, WI (US) 54235; Robert J. Harter, 4233 Cliffside Dr., La Crosse, WI (US) 54601; Tyler R. Harter, 4233 Cliffside Dr., La Crosse, WI (US) 54601

( * ) Notice: Subject to any disclaimer, the term of this patent is extended or adjusted under 35 U.S.C. 154(b) by 1246 days.

(21) Appl. No.: 10/813,421

(22) Filed: Mar. 30, 2004

(51) Int. Cl.
*G06Q 50/00* (2006.01)
*A61B 5/00* (2006.01)

(52) U.S. Cl. ............................................. 705/2; 705/3
(58) Field of Classification Search ................. 705/2–3
See application file for complete search history.

(56) References Cited

U.S. PATENT DOCUMENTS

| | | | | |
|---|---|---|---|---|
| 4,414,629 | A * | 11/1983 | Waite | 705/28 |
| 4,752,889 | A * | 6/1988 | Rappaport et al. | 706/11 |
| 5,486,999 | A * | 1/1996 | Mebane | 705/2 |
| 5,714,338 | A * | 2/1998 | Wai Fei et al. | 435/7.24 |
| 5,910,421 | A * | 6/1999 | Small et al. | 435/19 |
| 6,095,985 | A | 8/2000 | Raymond et al. | |
| 6,401,057 | B1 * | 6/2002 | Kadtke et al. | 702/189 |
| 6,756,032 | B1 * | 6/2004 | Tepper et al. | 424/9.8 |
| 6,879,970 | B2 | 4/2005 | Shiffman et al. | |
| 2002/0013538 | A1 * | 1/2002 | Teller | 600/549 |
| 2005/0234306 | A1 * | 10/2005 | Schulte et al. | 600/300 |
| 2006/0090215 | A1 * | 4/2006 | Buchanan et al. | 800/278 |

FOREIGN PATENT DOCUMENTS

WO      WO 03086052      * 10/2003

OTHER PUBLICATIONS

Berkow et al., The Merck Manual of Diagnosis and Therapy, 1992, Merck Research Laboratories, Sixteenth Edition, pp. 88-90, 328-331, 335-336, 650.*
Evans et al., A Computer Assisted Management Program for Antibiotics and Other Antiinfective Agents, Jan. 22, 1998, The New England Journal of Medicine, 338:232-238.*
Lowy, Medical Progress: *Staphylococcus aureus* Infections, Aug. 20, 1998, The New England Journal of Medicine, 339:520-532.*

(Continued)

*Primary Examiner*—C. Luke Gilligan
*Assistant Examiner*—Tran Nguyen
(74) *Attorney, Agent, or Firm*—bobharter.com; Robert J. Harter (57) ABSTRACT

A test method that helps identify foods that may be causing a reaction in an individual involves the individual entering into a computer a daily log of all the foods they routinely eat and any reactions that they may experience. The reactions may be headaches, fatigue, physical pain, depression, etc. The test method can be done without the individual having to follow any prescribed diet. After recording several weeks or months of data, the computer analyzes the data to determine if any significant mathematical correlations exist between a reaction and any of the foods, whereby a high positive correlation may suggest that the food is perhaps related to the reaction. In addition to food items, the method can analyze the correlation of other influencing agents such as environmental exposures, inhalants, menses, and stress.

33 Claims, 7 Drawing Sheets

OTHER PUBLICATIONS

Ciccarelli et al., Medicine in the Past Millennium, May 4, 2000, The New England Journal of Medicine, 342:1365-1367.*

Bates et al., Improving Safety with Information Technology, Jun. 19, 2003, The New England Journal of Medicine, 348:25. 2526-2534.*

Berkow et al., The Merck Manual of Diagnosis and Therapy, 1992, Merck Research Laboratories, Sixteenth Edition, pp. 88-90, 328-331, 335-336, 650.*

Evans et al., A Computer Assisted Management Program for Antibiotics and Other Antiinfective Agents, Jan. 22, 1998, The New England Journal of Medicine, 338:232-238.* www.phtcorp.com Published on Internet by Dec. 1, 2002.
www.weightbydate.com Published on Internet by Mar. 29, 2003.
www.betbyte.com Published on Internet by Feb. 19, 2003.
www.invivodata.com Published on Internet by Mar. 21, 2003.
www.symtrend.com Published on Internet by Aug. 24, 2003.

* cited by examiner

METHOD FOR IDENTIFYING ALLERGENS AND OTHER INFLUENCING AGENTS THAT MAY CAUSE A REACTION

BACKGROUND OF THE INVENTION

1. Field of the Invention

The subject invention generally pertains to a method of identifying allergens and other influencing agents that may cause a reaction in an individual and more specifically pertains to a software program for carrying out the method.

2. Description of Related Art

Many individuals (humans as well as other animals) may suffer various aliments and reactions due to their exposure to allergens or certain other adverse influencing agents. Such influencing agents may include foods (e.g., beverage, wheat, milk, medication, vitamins, food supplements, etc.), environmental exposures (mold, pollen, stress, etc.), and conditions such as constipation or a menstrual period. The reactions may include headaches, respiratory problems, skin problems, fatigue, constipation, abnormal blood pressure, depression, seizures, etc.

There are various techniques currently used to help identify allergens, foreign substances or other influencing agents that may adversely affect a particular individual. A skin prick test, for instance, is perhaps one of the most commonly used techniques. Although quite useful, such tests have some drawbacks. Skin prick tests typically involve a series of needle pricks that can be painful and frightening, particularly with younger children and some adults. Prick tests are not as valuable when trying to identify certain influencing agents such as sunlight, stress, and sleep loss. Moreover, skin tests are not as easily applied to pets and other non-human animals whose skin is covered with fur.

Before or in conjunction with a skin prick test, a patient may try an elimination diet to help identify the more likely causes of their reactions. An elimination diet involves systematically abstaining from certain foods over a given period. Each week, for instance, a person may eliminate one or more foods from their normal diet to see which foods may be causing the problem. Such a method, unfortunately, requires a lot of self-discipline and time. Elimination diets can take months or even years to complete, and sometimes they may never be completed if a person's tolerance to various foods changes over the years.

Also, the effectiveness of an elimination diet can be limited by the amount and variety of food that a person can consume in a given week (or other predetermined period). If a person, for instance, was free of any adverse reactions during a week when they abstained from milk, the person may believe they react to milk. During that same week, however, the person may have unknowingly avoided eating a hundred other foods, any one of which may be the real source of the problem. So, milk may not necessarily be the problem. If the person has a reaction after having milk the second week, the person may become even more convinced that milk is the problem even though the true adverse agent is actually one or more of those hundred other foods they avoided eating the first week but consumed the second week.

Consequently, there is a need for a reliable and painless way to help identify the influencing agents that may be causing an individual's adverse reactions, wherein the method can be used in conjunction with currently available methods of testing.

SUMMARY OF THE INVENTION

To provide an easy way to help identify allergens and other influencing agents that may be causing a reaction in an individual, it is an object of the invention to collect data on an individual's daily routine exposures and reactions, and mathematically interpret the data via a computer to identify which exposures most closely correlate to certain reactions.

Another object of some embodiments is to sort or prioritize a list of influencing agents according to their correlation with a certain reaction.

Another object of some embodiments is to facilitate the gathering of data by displaying on a computer monitor a list of possible influencing agents and/or reactions from which a user can simply select certain items via a click of a mouse.

Another object of some embodiments is to plot, over a period of days, months or years, data collected on an individual's daily routine exposures and reactions, and display the plot on a computer monitor so that both immediate and delayed responses to various exposures can be readily identified.

Another object of some embodiments is assign magnitude values to various exposures and reactions experienced by an individual.

Another object of some embodiments is to compute a correlation between an exposure and a reaction, wherein the correlation is at least partially based on whether a menstrual period occurred.

Another object of some embodiments is to compute a correlation between an exposure and a reaction, wherein the exposure is a food.

Another object of some embodiments is to compute a correlation between an exposure and a reaction, wherein the exposure is an activity of an individual. Examples of such an activity include, but are not limited to, exercise and social interaction.

Another object of some embodiments is to compute a correlation between an exposure and a reaction, wherein the exposure is an individual's amount of sleep.

Another object of some embodiments is to compute a correlation between an environmental exposure and a reaction. Examples of environmental exposures include, but are not limited to, pollen count, mold count, ragweed count, humidity, and barometric pressure.

Another object of some embodiments is to input or download into a computer Internet accessible data that relates to an environmental exposure.

Another object of some embodiments is to compute a correlation between an exposure and a reaction, wherein the reaction is physical pain.

Another object of some embodiments is to compute a correlation between an exposure and a reaction, wherein the reaction is respiratory-related.

Another object of some embodiments is to compute a correlation between an exposure and a reaction, wherein the reaction is skin-related.

Another object of some embodiments is to compute a correlation between an exposure and a reaction, wherein the reaction is blood pressure that has gone beyond a predetermined normal range.

Another object of some embodiments is to compute a correlation between an exposure and a reaction, wherein the reaction is fatigue.

Another object of some embodiments is to compute a correlation between an exposure and a reaction, wherein the reaction is mentally related.

Another object of some embodiments is to compute a correlation between an exposure and a reaction, wherein the reaction is a seizure.

Another object of some embodiments is to compute a correlation between an exposure and a reaction, wherein the reaction is an emotional disturbance.

Another object of some embodiments is to compute a correlation between an exposure and a reaction, wherein there is a time delay of one or more days between the time of the exposure and when the reaction occurred.

Another object of some embodiments is to identify the ingredients of a food and determine a correlation between a reaction and the various ingredients.

Another object of some embodiments is to assign a confidence value to a correlation value, wherein the confidence value provides some indication of the correlation value's reliability.

One or more of these and/or other objects of the invention are provided by a method that helps identify influencing agents that may be causing a reaction in an individual. The method involves collecting data on an individual's daily exposures and reactions, and mathematically interpreting the data via a computer to identify which exposures most closely correlate to certain reactions.

DESCRIPTION OF THE PREFERRED EMBODIMENT

FIGS. 1-7 illustrate a test method 10 that uses a computer 12 (desktop, laptop, handheld, Palm Pilot, etc.), a computer monitor 14 or display, a computer keyboard 16, a computer mouse 18 and an appropriate computer software program 20 to help identify a suspect influencing agent 22 that may be causing an adverse reaction 24 in an individual 26. Over a period of months, for example, individual 26 can enter into computer 12 his daily food consumption and any reaction that he's been experiencing periodically. Program 20 then controls computer 12 to calculate how closely each food item correlates with the reaction. A food item having a high positive correlation indicates that the food item may be causing the reaction and that further tests (e.g., skin prick test) may be warranted to determine whether the food item and reaction actually have a cause and effect relationship.

The term, "influencing agent" refers to anything that can trigger, cause or lead to a reaction in individual 26. Examples of influencing agents include, but are not limited to, food, drugs, medication, environmental exposures, barometric pressure, stress, sunlight, amount of sleep, inhalants, chemicals, plants, beverages, microorganisms, amount of exercise, etc. The term, "reaction" refers to any response by individual 26 as a possible result of being exposed to or experiencing an influencing agent. Examples of a reaction include, but are not limited to, a headache, migraine, rash, hives, fatigue, breathing disorder, tinnitus, physical pain, change in blood pressure, diminished alertness, dizziness, seizure, mental or emotional disturbance, congestion, sneezing, coughing, blemishes, itching, dermatonosis, etc. For simplicity the term, "influencing agent" broadly encompass not only the physical influencing agent such as actual corn itself, but also encompasses a data entry, name, or other representation of corn. In other words, entering corn into the computer means entering a word or another identifier of corn in the computer and not physically stuffing corn into the computer. The same applies to the term, "reaction." The term, "individual" refers to any human animal or even a non-human animal such as a pet. The term, "correlation" and derivatives thereof refer to a value or symbol that provides at least some indication of how closely the occurrence of one item relates to the occurrence of another. Test method 10 is perhaps best understood with reference to the following example.

Individual 26 utilizes test method 10 to enter which influencing agents he was exposed to and which reactions were exhibited for three one-day periods. Computer monitor 14 of FIG. 1 displays a plurality of possible influencing agents 28 and a plurality of possible reactions 30 that individual 26 can choose from by simply mouse-clicking 36. Additions to the plurality of possible influencing agents 28 and the plurality of reactions 30 can be entered via keyboard 16 or prewritten in the software program 20.

Figure 1:
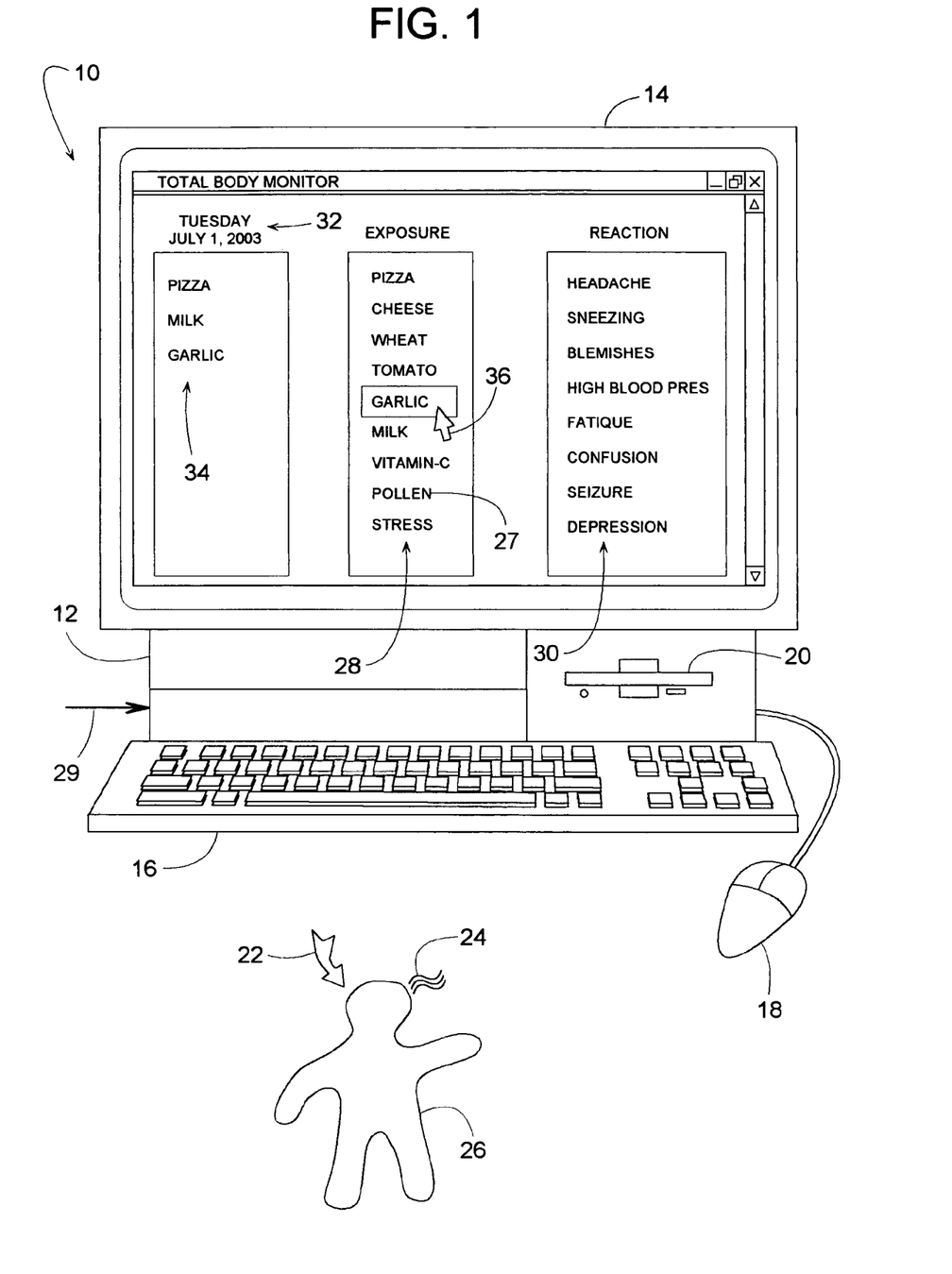
FIG. 1 is a front view of a computer display being used in a test method for assisting in identifying allergens and other influencing agents that may be related to a reaction in an individual, wherein the display shows a first page where data is entered for a first period, Tuesday.

For a first period 32, Tuesday, individual 26 (or a user representative thereof) enters a first plurality of influencing agents 34 to which individual 26 has been exposed during period 32. Individual 26, for example, can enter that he consumed pizza, milk and garlic on Tuesday. The plurality of possible influencing agents 28 can be entered via keyboard 16 or by some other appropriate means. Internet accessible data, such as pollen count 27, for example, can be acquired for a particular region (e.g., identified by zip code), and downloaded 29 into computer 12 by using a conventional modem. Pollen count 27 can then be displayed along with the other possible influencing agents 28. The first plurality of influencing agents 34 for period 32 can be entered via keyboard 16, or influencing agents 34 can be entered by simply mouse-clicking 36 on selected possible influencing agents 28. For this particular day, individual 26 experienced none of the plurality of reactions 30.

Figure 2:
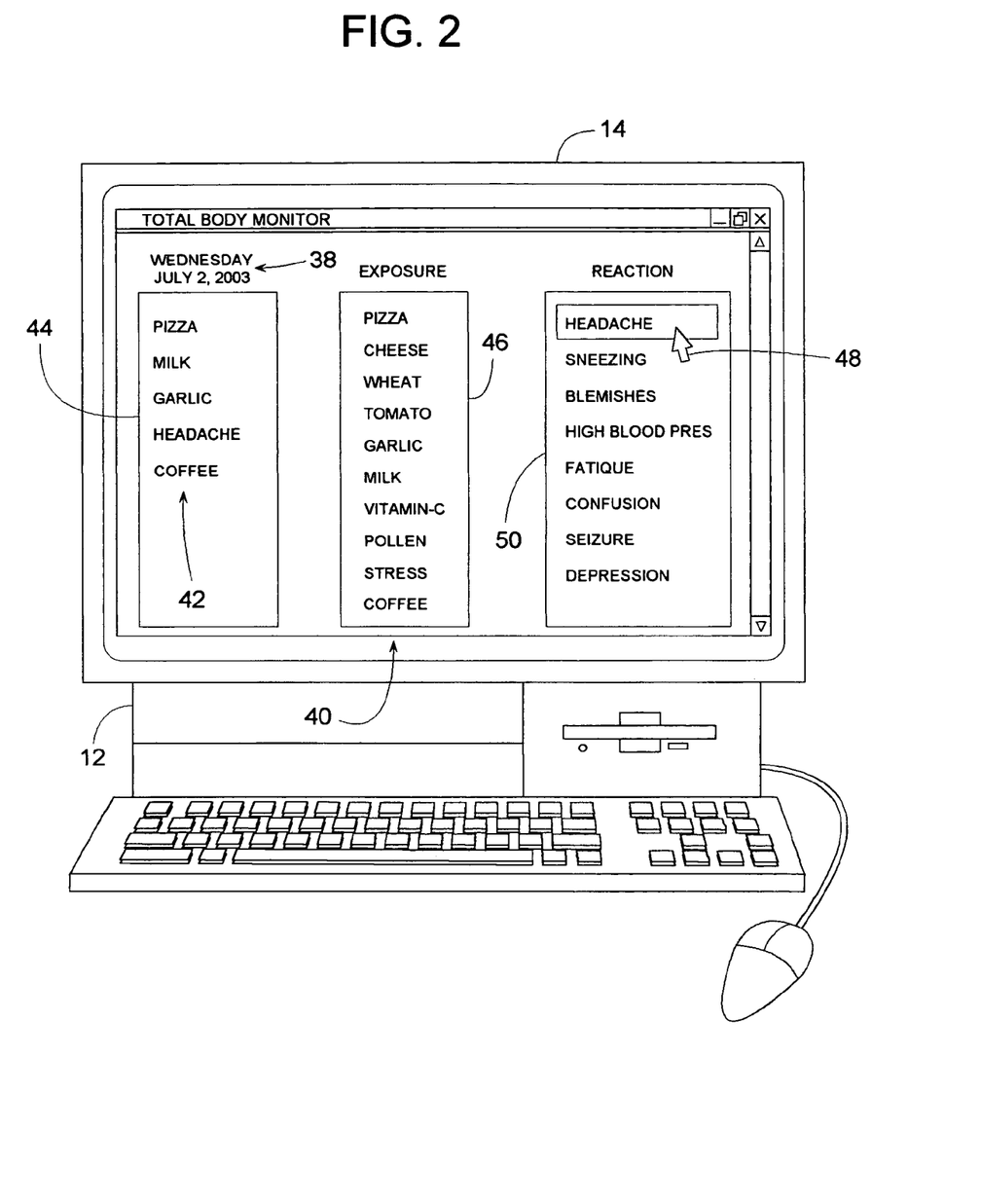
FIG. 2 is similar to FIG. 1 but showing a second page where data is entered for a second period, Wednesday.

For a second period 38, Wednesday, monitor 14 of FIG. 2 displays a larger plurality of possible influencing agents 40, as "coffee" has been added to the original plurality of possible influencing agents 28 of FIG. 1. In this example, Wednesday was the first day that individual 26 consumed coffee, so coffee needed to be added to the list via keyboard 16. After Wednesday, coffee will continue to automatically appear on the list of possible influencing agents from which individual 26 may choose and enter by mouse-clicking on that item rather than having to retype "coffee" whenever it is consumed. On Wednesday, individual 26 consumed pizza, milk, garlic and coffee, which comprise a second plurality of influencing agents 42 that were entered into box 44 by selectively mouse-clicking on those items in box 46. On this day, individual 26 also experienced a headache, which individual 26 entered into box 44 by selectively mouse-clicking 48 on "headache" in box 50.

Figure 3:
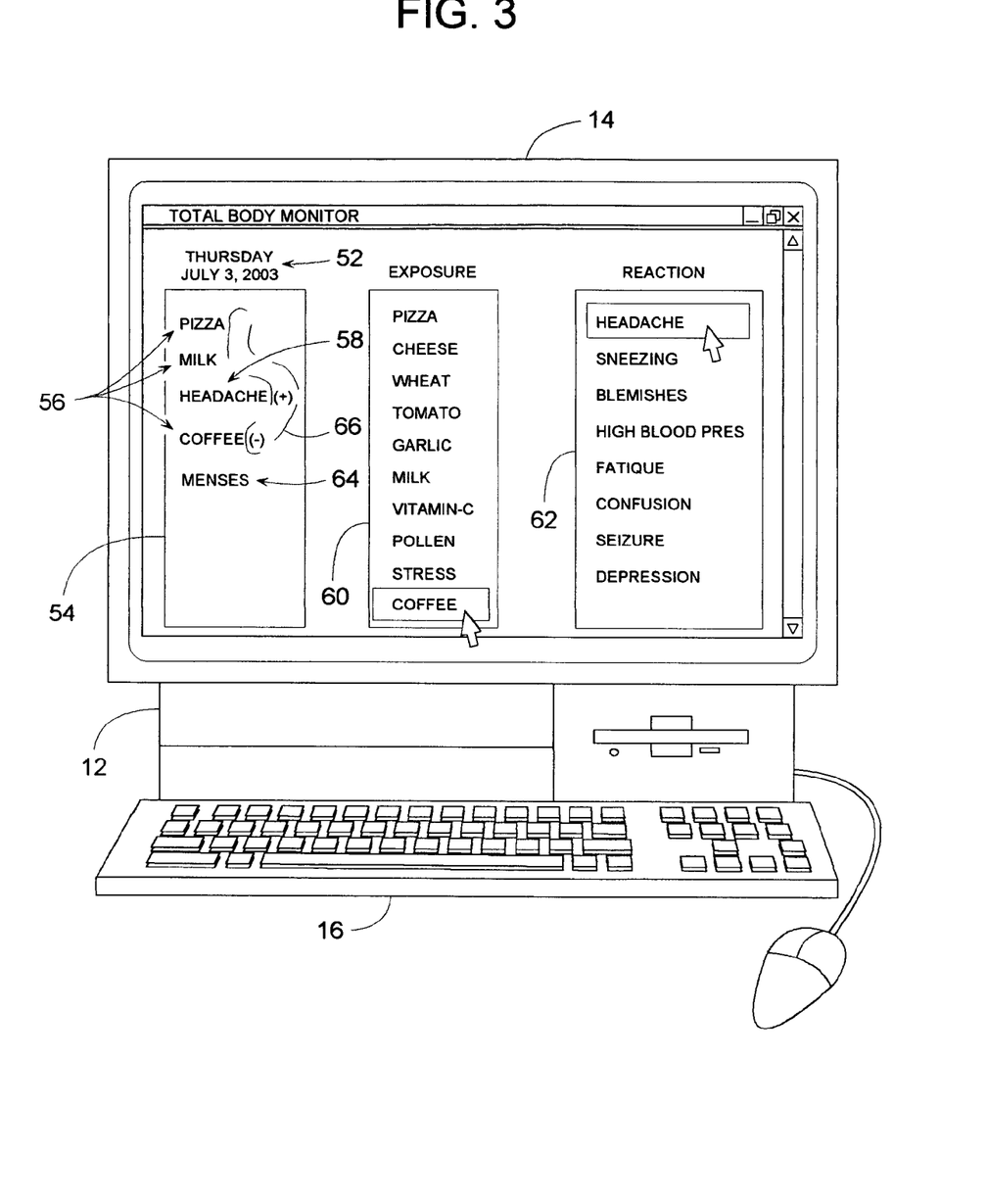
FIG. 3 is similar to FIG. 1 but showing a third page where data is entered for a third day, Thursday.

For a third period 52, Thursday, monitor 14 of FIG. 3 displays in box 54 a plurality of influencing agents 56 (pizza, milk, and coffee) and a headache reaction 58 that individual 26 experienced that day and entered by mouse-clicking on the appropriate items in boxes 60 and 62. Box 54 also shows that individual 26 experienced a menses 64 (i.e., in the case where individual 26 is a female of course). The "menstrual period" can be entered in any appropriate manner, such as by mouse-clicking on that item in box 60 or entering it via keyboard 16.

FIG. 3 also shows how a magnitude value 66 can be assigned to an influencing agent or a reaction. The magnitude values can be helpful (but not absolutely necessary) in identifying which influencing agents are most likely causing a certain reaction. For an influencing agent, a magnitude value can represent how much the individual consumed or to what extent the individual was exposed. In some embodiments of the invention, the magnitude value of an influencing agent can be assigned one of three values: a plus sign, a minus sign, or a blank, which represent above average exposure, below average exposure, and an average exposure, respectively. For the illustrated example, "coffee" has been assigned a "minus" magnitude value, while the rest of the influencing agents have been assigned a "blank" or average magnitude value.

Similarly, a magnitude value can indicate the severity of a reaction. A reaction, for example, can be assigned a plus sign, minus sign, or blank, which represent a reaction that is severe, mild, or average, respectively.

In a currently preferred embodiment of the invention, the magnitude value of an influencing agent or a reaction is assigned by right-mouse-clicking on the item to display a dropdown menu from which a magnitude value can be selected and assigned to that item.

Although FIGS. 1-3 represent just three days of entering data, the process really continues for weeks or months to obtain meaningful results. Once the data is collected, computer 12 responds to program 20 by computing a correlation between each possible influencing agent and each reaction.

Figure 4:
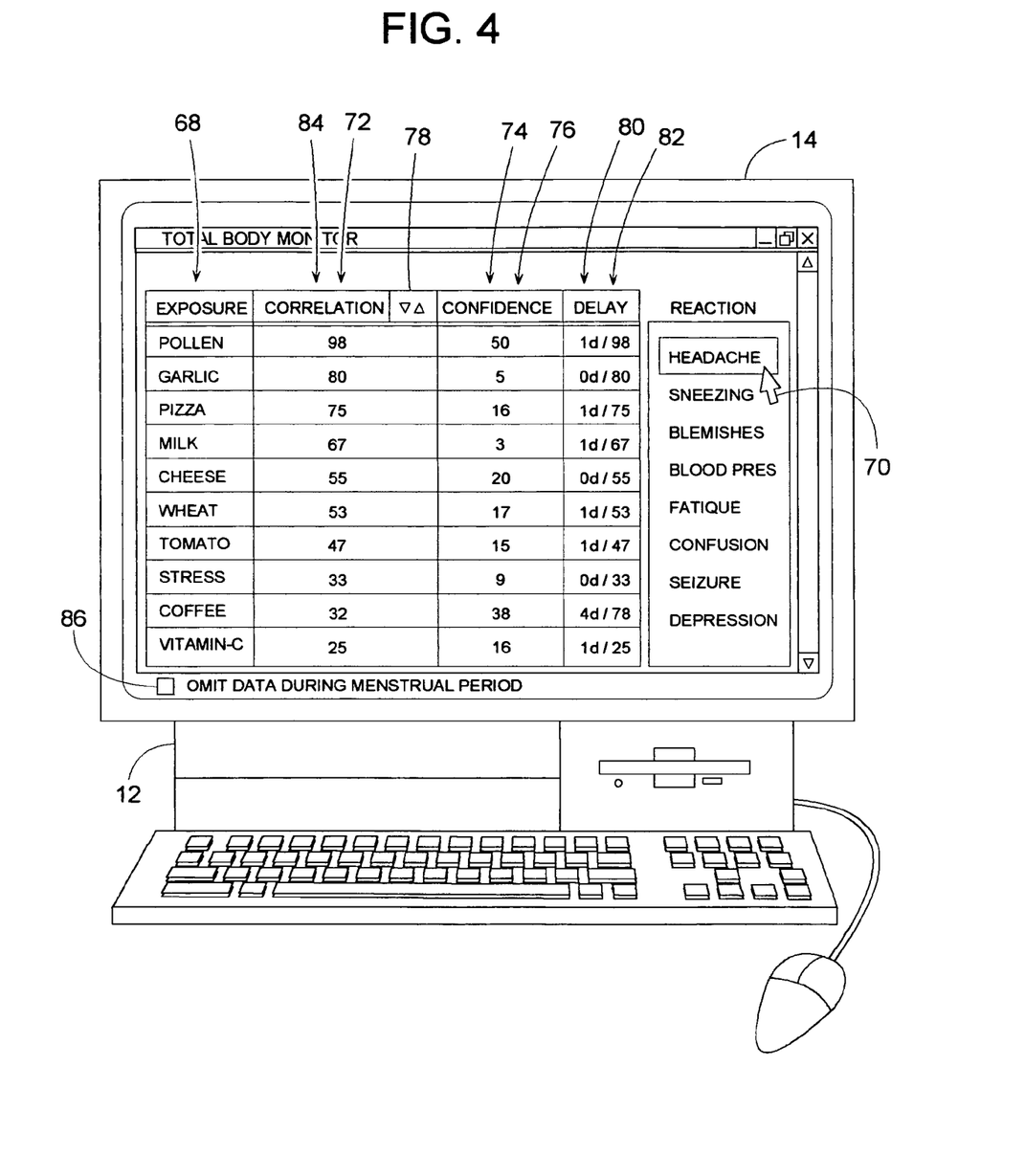
FIG. 4 is similar to FIG. 1 but showing a fourth page that displays a list of correlation values, confidence values, and delayed reaction values.

Individual 26 can use the display of FIG. 4 to help identify which of a plurality of influencing agents 68 most closely correlate with a particular reaction. To determine how well each influencing agent correlates to a headache, for instance, individual 26 mouse-clicks 70 on "headache," and computer 12 responds by displaying a plurality of correlations 72 that correspond to the plurality of influencing agents 68 as they relate to the headache reaction. Likewise, mouse-clicking on any of the other reactions, sneezing, blemishes, blood pressure, etc., would generate their own plurality of correlations that show how well each of the influencing agents correlate to that reaction.

The higher the positive correlation value, the more suspect the respective influencing agent may become as being the cause of the reaction. For the example of FIG. 4, "pollen" may be considered a suspect influencing agent as it has a positive correlation of 98% with respect to the headache reaction. Even though it would be subjective to label a correlation value as high or low, a correlation value for a particular influencing agent can still be useful, especially when the values are compared to those of other influencing agents. In some cases, coincidental or otherwise, high correlations may exist between an influencing agent and a reaction even though the agent may actually have no cause and effect relationship whatsoever. So, this testing method serves as a guide or an aid rather than as a conclusive test or diagnosis.

Computing a correlation can be carried out using any of a variety of suitable algorithms or mathematical equations that are well known to those skilled in the art of statistical analysis. For example, a correlation between an influencing agent and a reaction may simply be the percentage of times that the reaction occurred within one day after the consumption or exposure of the influencing agent.

In some cases, a confidence value 74 may be assigned to a correlation value where the confidence value provides at least some indication of the correlation value's reliability. Confidence values can be computed in various conventional ways. Each confidence value in column 76 of FIG. 4, for example, is simply a total number of occurrences of the influencing agent for which the correlation has been computed.

To assist in interpreting the data, mouse-clicking on a soft key 78 can sort the displayed data by correlation value, confidence value, a delay value 80, alphabetization of influencing agents, etc.

In some embodiments of the invention, test method 10 may also help in identifying possible delayed reactions where a reaction may occur a few or several days after individual 26 is exposed to a certain influencing agent. Column 82 of FIG. 4, for example, displays a list of delayed values 80 where each value provides a delay period and a correlation value separated by a slash. The delay period represents the time it takes for a reaction to occur after being triggered by an influencing agent. The influencing agent of coffee, for example, has a correlation of 78% when compared to headache reactions that occur four days after the consumption of coffee. Otherwise, the correlation of coffee and an immediate headache (i.e., a headache that occurs within a day of the consumption) is 32%.

If responses occur within one day, the delayed values of column 82 can be determined in a manner similar to the way the correlations 72 of column 84 are computed. However, if the responses occur more than one day later, then a series of correlations are first computed for each agent-reaction pair, wherein the series includes a correlation value for a zero to one-day delay (which is already displayed in column 84), a two-day delay, a three-day delay, a four-day delay, etc. Of the delayed values, the one with the highest correlation is displayed in column 82 alongside the period of delay. For the example of FIG. 4, it appears that only coffee may trigger a delayed headache response (four-day delay), while all the other influencing agents tend to correlate more with an immediate headache response (within one day).

Figure 5:
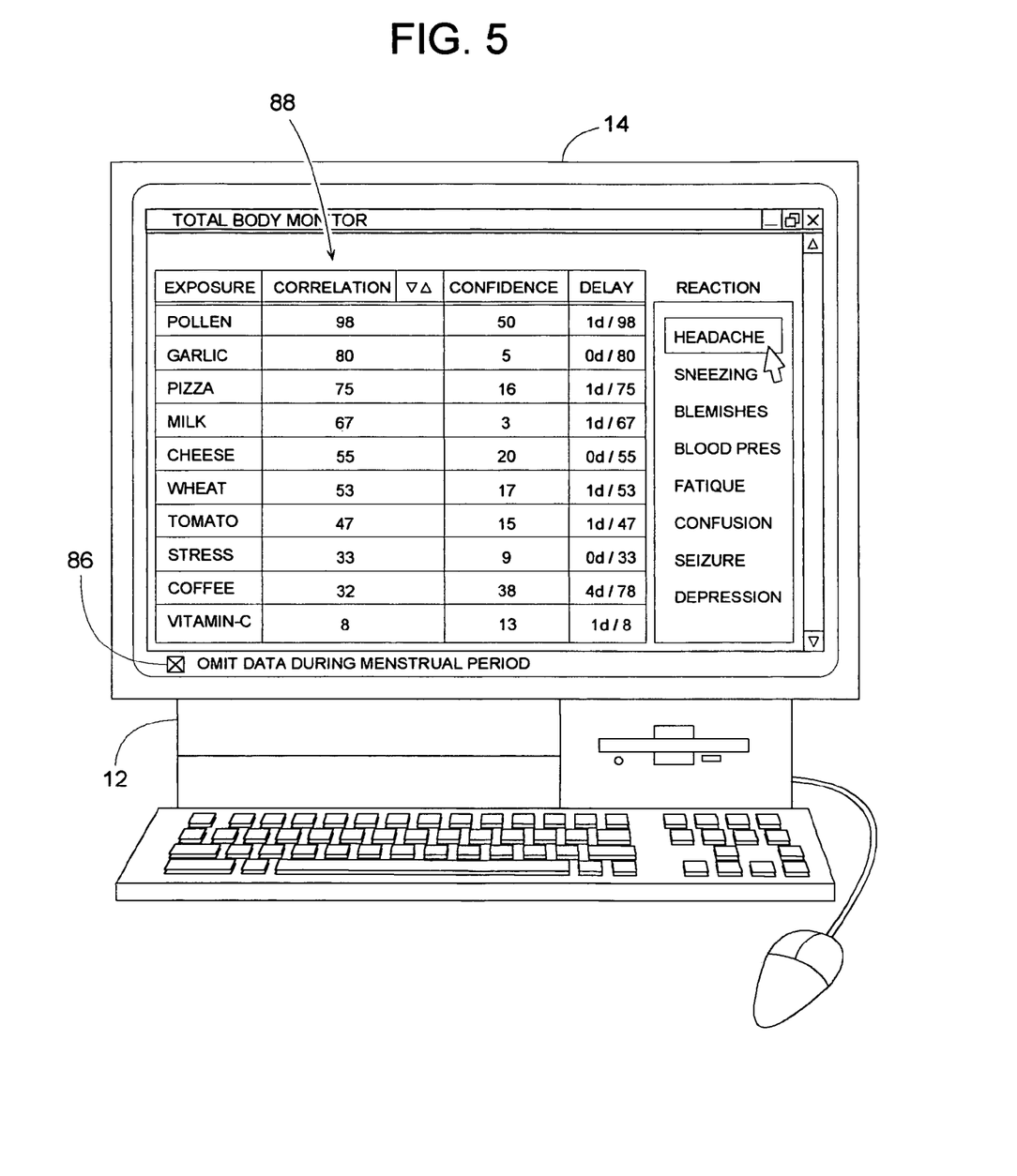
FIG. 5 is similar to FIG. 1 but showing a fifth page that illustrates how omitting data collected during a menstrual period can affect a correlation value.

In some cases, a female's menstrual period may adversely affect a calculated correlation between an influencing agent and a reaction. If a woman, for example, always experiences a headache during her menstrual period, and she drinks more coffee during that time, then program 20 may improperly determine a high correlation between coffee and headaches. To adjust for this, program 20 provides a checkbox 86 that can be selectively checked with a mouse-click. Checking or not checking box 86 determines which of two computations that computer 12 will carry out to compute the plurality of correlations (correlations 72 of FIG. 4 or correlations 88 of FIG. 5). By checking the box 86, as shown in FIG. 5, program 20 disregards the data collected during the subject's menstrual period, so the computed correlation values 88 will only be based on days where "menses" was not entered in box 54 of FIG. 3.

Figure 6:
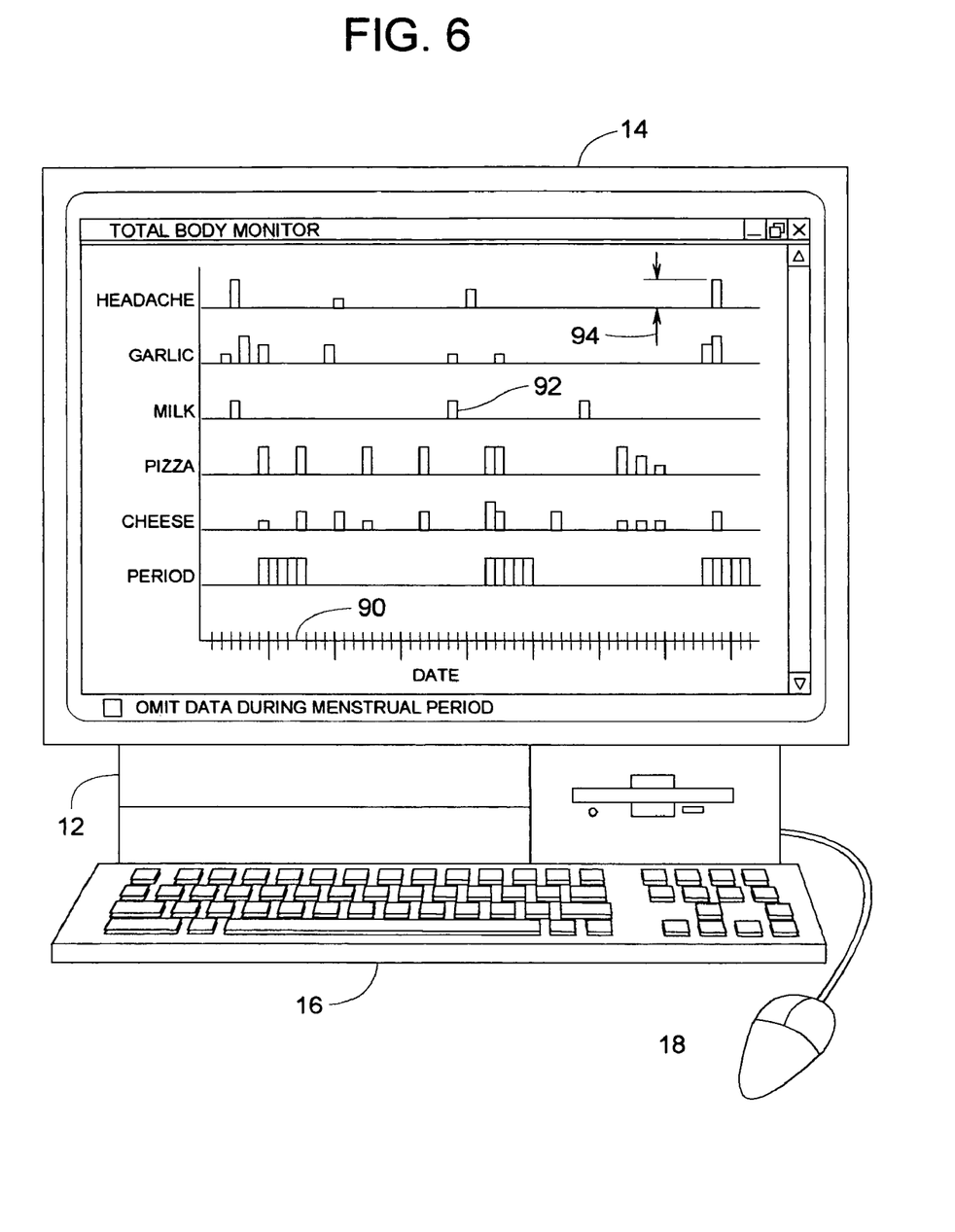
FIG. 6 is similar to FIG. 1 but showing a sixth page where the data is displayed graphically.

The correlation between a reaction and various influencing agents can also be analyzed by plotting the occurrence of each over a common time scale 90 (e.g., units of days), as shown in FIG. 6. Each vertical bar (e.g., bar 92) represents an occurrence of a reaction or an influencing agent, and each bar's height (e.g., dimension 94) represents the item's magnitude value. The method of selecting which reactions and/or influencing agents are plotted can be carried out in any suitable manner via mouse 18 or keyboard 16.

Figure 7:
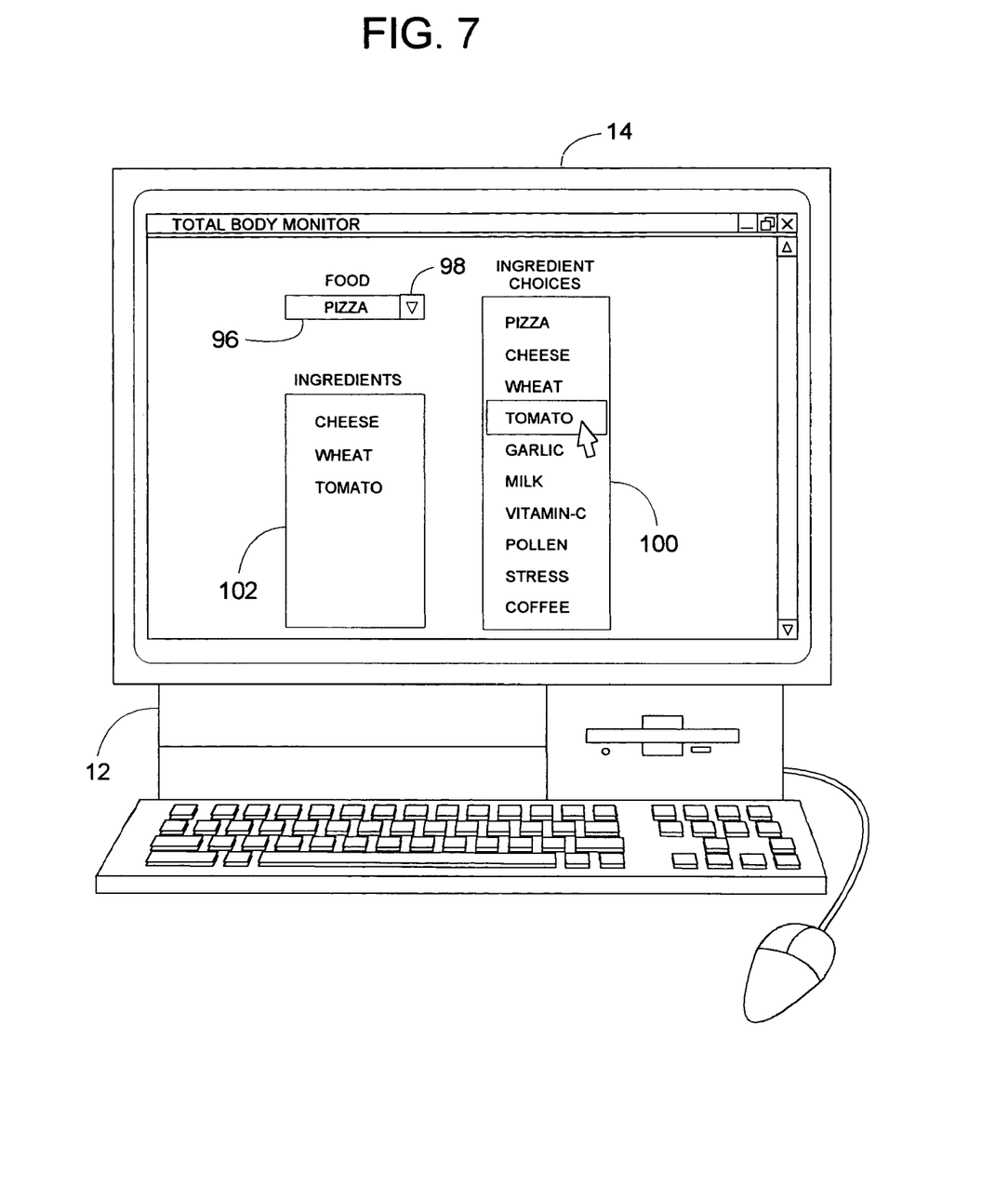
FIG. 7 is similar to FIG. 1 but showing a seventh page where an ingredients list is defined for a food item.

In some embodiments of the invention, testing method 10 takes into account a food item's ingredients and considers those ingredients as influencing agents in themselves. In FIG. 7, for example, monitor 14 displays a page where a food item, such as pizza, is entered into a block 96 by way of mouse-clicking on a dropdown menu 98. Then, in another block 100, a user can mouse-click on the various pizza ingredients, such as cheese, wheat, tomato, etc. Selectively clicking on ingredients in block 100 defines an ingredients list in a block 102. Then, whenever individual 26 consumes pizza, program 20 records that individual 26 not only consumed pizza but also consumed cheese, wheat and tomato as well. Individual correlation values can then be computed for pizza, cheese, wheat, and tomato, which can be useful information as one or more of those ingredients may be consumed alone or as an ingredient of yet another food.

It should be appreciated by those skilled in the art that the screen displays of FIGS. 1-7 do not have to be exactly as shown to achieve the desired results of the invention. The illustrated screen displays, or ones similar thereto, are readily achieved using conventional computer programming practice. Program 20 is readily created using any of a variety of readily available and well-known computer programs including, but not limited to, Visual Basic, C++, JAVA, Microsoft Excel, etc. It should also be appreciated by those skilled in the art that navigation from one screen to another is readily achieved in various conventional ways including, but not limited to, mouse-clicking softkeys (e.g., "Forward" and "Back" buttons), arrow keys on keyboard 16, "Page Up" and "Page Down" keys on keyboard 16, etc. Although the invention is described with reference to a preferred embodiment, it should be appreciated by those skilled in the art that various modifications are well within the scope of the invention. Therefore, the scope of the invention is to be determined by reference to the claims that follow.

We claim:

1. A method of using a computer and a computer display for identifying a suspect influencing agent that may be causing a reaction in an individual, wherein the suspect influencing agent is one of a plurality of possible influencing agents, the method comprising:

displaying the plurality of possible influencing agents on the computer display;

displaying the reaction on the computer display;

for a first period, selecting a first plurality of influencing agents from the plurality of possible influencing agents, wherein the individual was exposed to the first plurality of influencing agents during the first period, wherein the step of selecting the first plurality of influencing agents is via the computer;

for a second period following the first period, selecting a second plurality of influencing agents from the plurality of possible influencing agents, wherein the individual was exposed to the second plurality of influencing agents during the second period, wherein the step of selecting the second plurality of influencing agents is via the computer;

selecting, via the computer, the reaction that the individual experienced during at least one of the first period, the second period, and a third period, wherein the third period follows the second period;

computing, with the computer, a plurality of correlations corresponding to the plurality of possible influencing agents as each of the plurality of possible influencing agents relate to the reaction;

and based on the plurality of correlations, determining, with the computer, and displaying the suspect influencing agent.

2. The method of claim 1, wherein at least one of the plurality of possible influencing agents is a food.

3. The method of claim 2, further comprising specifying an ingredient for the food, and computing a correlation between the ingredient and the reaction.

4. The method of claim 1, further comprising sorting the plurality of possible influencing agents based on the plurality of correlations.

5. The method of claim 1, further comprising adding, after the first period, an additional possible influencing agent to the plurality of possible influencing agents.

6. The method of claim 1, wherein the step of selecting the first plurality of influencing agents from the plurality of possible influencing agents is performed by mouse-clicking on at least some of the plurality of possible influencing agents.

7. The method of claim 1, wherein the step of selecting the reaction that the individual experienced involves mouse-clicking on the reaction.

8. The method of claim 1, further comprising entering a plurality of reactions into the computer wherein the plurality of reactions includes the reaction.

9. The method of claim 1, further comprising displaying a single view of the reaction and the plurality of possible influencing agents on the computer display, wherein the single view assists in selecting the reaction and assists in selecting the first plurality of influencing agents.

10. The method of claim 1, further comprising plotting a graph of the suspect influencing agent and the reaction versus time, and displaying the graph on the computer display to help illustrate how well the suspect influencing agent and the reaction correlate.

11. The method of claim 1, further comprising assigning a magnitude value to the reaction.

12. The method of claim 1, further comprising assigning a magnitude value to each of the first plurality of influencing agents.

13. The method of claim 1, wherein the plurality of correlations includes a correlation that reflects the likelihood that the suspect influencing agent may cause a future reaction.

14. The method of claim 1, wherein the plurality of correlations are based selectively on a first computation and a second computation, the first computation and the second computation are differentiated from each other by how the first computation and the second computation account for a menstrual period.

15. The method of claim 1, further comprising computing a time-delayed correlation between the suspect influencing agent and the reaction.

16. The method of claim 1, further comprising assigning a plurality of confidence values to the plurality of correlations.

17. The method of claim 1, wherein the first period and the second period are sequential days.

18. The method of claim 1, wherein the suspect influencing agent is an allergen.

19. The method of claim 1, wherein the suspect influencing agent is an environmental exposure.

20. The method of claim 1, wherein the reaction is a physical pain.

21. The method of claim 1, wherein the reaction is respiratory-related.

22. The method of claim 1, wherein the reaction is skin-related.

23. The method of claim 1, wherein the reaction is blood pressure.

24. The method of claim 1, wherein the reaction is fatigue.

25. The method of claim 1, wherein the reaction is mentally-related.

26. The method of claim 1, wherein the reaction is a seizure.

27. The method of claim 1, wherein the reaction is an emotional disturbance.

28. The method of claim 1, wherein the suspect influencing agent is an activity of the individual.

29. The method of claim 1, wherein the suspect influencing agent relates to an amount of sleep of the individual.

30. The method of claim 1, further comprising downloading into the computer Internet accessible data that relates to an environmental exposure, and computing a correlation between the environmental exposure and the reactions wherein the step of determining and displaying the suspect influencing agent is further based on the correlation between the environmental exposure and the reaction.

31. A method of using a computer and a computer display for identifying a suspect influencing agent that may be causing a reaction in an individual, wherein the suspect influencing agent is one of a plurality of possible influencing agents, the method comprising:
   entering into the computer the plurality of possible influencing agents;
   displaying the plurality of possible influencing agents on the computer display;
   entering the reaction into the computer;
   displaying the reaction on the computer display;
   for a first period, selecting, with the computer, a first plurality of influencing agents from the plurality of possible influencing agents, wherein the individual was exposed to the first plurality of influencing agents during the first period, wherein the step of selecting the first plurality of influencing agents from the plurality of possible influencing agents is performed by mouse-clicking on at least some of the plurality of possible influencing agents;
   for a second period following the first period, selecting, with the computer, a second plurality of influencing agents from the plurality of possible influencing agents, wherein the individual was exposed to the second plurality of influencing agents during the second period, wherein the step of selecting the second plurality of influencing agents from the plurality of possible influencing agents is performed by mouse-clicking on at least some of the plurality of influencing agents;
   selecting, via the computer, the reaction that the individual experienced during at least one of the first period, the second period, and a third period, wherein the third period follows the second period;
   computing, with the computer, a plurality of correlations corresponding to the plurality of possible influencing agents as each of the plurality of possible influencing agents relate to the reaction;
   adding, with the computer, after the first period, an additional influencing agent to the plurality of possible influencing agents;
   and based on the plurality of correlations, determining, with the computer, and displaying, with the computer, the suspect influencing agent.

32. A method of using a computer and a computer display for identifying a suspect influencing agent that may be causing a reaction in an individual, the method comprising:
   entering into the computer a plurality of possible influencing agents, wherein the plurality of possible influencing agents includes the suspect influencing agent, and wherein at least one of the plurality of possible influencing agents is a food;
   displaying the plurality of possible influencing agents on the computer display;
   entering the reaction into the computer;
   displaying the reaction on the computer display;
   for a first period, selecting, with the computer, a first plurality of influencing agents from the plurality of possible influencing agents, wherein the individual was exposed to the first plurality of influencing agents during the first period, wherein the step of selecting the first plurality of influencing agents from the plurality of possible influencing agents is performed by mouse-clicking on at least some of the plurality of possible influencing agents;
   for a second period following the first period, selecting, with the computer, a second plurality of influencing agents from the plurality of possible influencing agents, wherein the individual was exposed to the second plurality of influencing agents during the second period, wherein the step of selecting the second plurality of influencing agents from the plurality of possible influencing agents is performed by mouse-clicking on at least some of the plurality of possible influencing agents;
   selecting, with the computer, the reaction that the individual experienced during at least one of the first period, the second period, and a third period, wherein the third period follows the second period, wherein the step of selecting the reaction is performed by mouse-clicking on the reaction;
   computing, with the computer, a plurality of correlations corresponding to the plurality of possible influencing agents, wherein the plurality of correlations reflect the likelihood that the plurality of possible influencing agents will cause a future reaction;
   adding, with the computer, after the first period, an additional influencing agent to the plurality of possible influencing agents;
   sorting, with the computer, the plurality of possible influencing agents based on the plurality of correlations;
   plotting a graph of the suspect influencing agent and the reaction versus time, and displaying the graph on the computer display to help illustrate how well the suspect influencing agent and the reaction correlate;
   assigning a magnitude value to the reaction;
   and displaying the magnitude value on the computer display.

33. A method of identifying a suspect influencing agent, comprising:
   storing a plurality of possible influencing agents into a computer;
   storing a plurality of reactions into the computer;
   selecting, with the computer, a plurality of possible influencing agents from the stored possible influencing agent, wherein an individual was exposed to the selected possible influencing agents;
   selecting, with the computer, a reaction from the plurality of stored reactions, wherein the individual experienced the selected reaction after exposure to the selected possible influencing agents;
   computing, with the computer, a correlation between each one of said selected possible influencing agents and the selected reaction;
   determining, with the computer, the possible influencing agent having the highest computed correlation from the plurality of computed correlations;
   displaying the determined possible influencing agent having the highest computed correlation as the suspect influencing agent suspected of causing the reaction in the individual.

* * * * *